United States Patent [19]
Hougen

[11] Patent Number: 5,890,998
[45] Date of Patent: Apr. 6, 1999

[54] PORTABLE PERSONAL BREATHING APPARATUS

[76] Inventor: Everett Douglas Hougen, 5463 Sugarbush, Flint, Mich. 48501

[21] Appl. No.: 16,775

[22] Filed: Jan. 30, 1998

Related U.S. Application Data

[63] Continuation of Ser. No. 386,375, Feb. 10, 1995, abandoned.

[51] Int. Cl.$^6$ .................................................. A63B 23/18
[52] U.S. Cl. .............................................. 482/13; 601/41
[58] Field of Search ......................... 482/13; 128/200.24; 601/41, 42, 43, 44; 84/93, 465, 466, DIG. 14

[56] References Cited

U.S. PATENT DOCUMENTS

| | | |
|---|---|---|
| 3,079 | 5/1843 | Rose . |
| D. 321,227 | 10/1991 | Norell . |
| 515,637 | 2/1894 | Wilhide . |
| 635,232 | 10/1899 | Carroll . |
| 737,008 | 8/1903 | Nichol . |
| 856,432 | 6/1907 | Thomson ................................... 482/13 |
| 940,735 | 11/1909 | Schaeffer et al. . |
| 1,295,118 | 2/1919 | Canaday ..................................... 482/13 |
| 1,392,700 | 10/1921 | Oyen . |
| 2,292,474 | 8/1942 | Paxton . |
| 3,298,362 | 1/1967 | Lippitt, Jr. et al. . |
| 3,333,844 | 8/1967 | Jurschak . |
| 3,810,461 | 5/1974 | McCormick . |
| 3,826,247 | 7/1974 | Ruskin et al. . |
| 3,863,914 | 2/1975 | O'Connor . |
| 3,908,987 | 9/1975 | Boehringer . |
| 3,949,984 | 4/1976 | Navara . |
| 4,025,070 | 5/1977 | McGill et al. . |
| 4,054,134 | 10/1977 | Kritzer . |
| 4,062,358 | 12/1977 | Kritzer . |
| 4,158,360 | 6/1979 | Adams . |
| 4,221,381 | 9/1980 | Ericson . |
| 4,275,722 | 6/1981 | Sorensen . |
| 4,291,704 | 9/1981 | Petty et al. . |
| 4,345,605 | 8/1982 | Gereg . |
| 4,365,628 | 12/1982 | Hodel ................................... 128/205.12 |
| 4,403,616 | 9/1983 | King . |
| 4,444,202 | 4/1984 | Rubin et al. . |
| 4,473,082 | 9/1984 | Gereg . |
| 4,533,137 | 8/1985 | Sonne . |
| 4,601,465 | 7/1986 | Roy . |
| 4,635,647 | 1/1987 | Choksi . |
| 4,739,987 | 4/1988 | Nicholson . |
| 4,770,413 | 9/1988 | Green . |
| 4,854,574 | 8/1989 | Larson et al. . |
| 4,973,047 | 11/1990 | Norell . |
| 4,981,295 | 1/1991 | Belman et al. . |
| 5,018,517 | 5/1991 | Liardet . |
| 5,154,167 | 10/1992 | Hepburn . |
| 5,165,393 | 11/1992 | Kawaguchi . |
| 5,193,529 | 3/1993 | Labaere . |

*Primary Examiner*—Jeanne M. Clark
*Attorney, Agent, or Firm*—Howard & Howard

[57] ABSTRACT

A respiratory exercise apparatus and method for providing resistance and percussion during inspiration and expiration. The apparatus includes a main body having an inner cavity, an orifice in communication with the inner cavity, and at least one aperture in communication with the inner cavity. A member is disposed and is movable relative to the main body. Pursuant to the method, upon movement of the member, the aperture in the main body is opened and closed. In one embodiment, the member has a plurality of circumferentially-spaced apertures which can be of different sizes. The user can select different size apertures to align to provide varying degrees of resistance to inspiration and expiration. By moving the member during inspiration and expiration, the apertures are sequentially aligned with the at least one aperture in the main body, providing a percussion effect. The user can control movement of the member with a lever pivotally disposed within a mouthpiece disposed over the orifice in the main body. The inner end of the lever engages the member. When the user closes the jaw muscles on the mouthpiece to press the lever downward, the lever pivots and rotates the member. When the user opens the jaw muscles, the member returns to the original position.

39 Claims, 6 Drawing Sheets

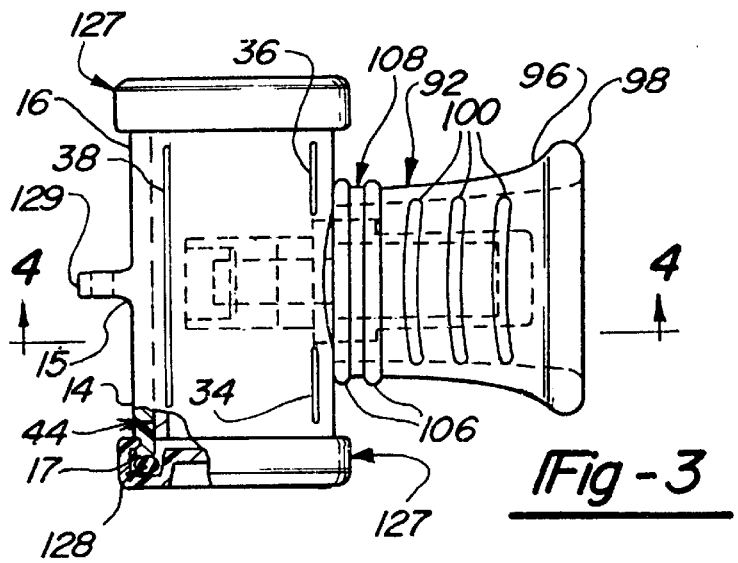
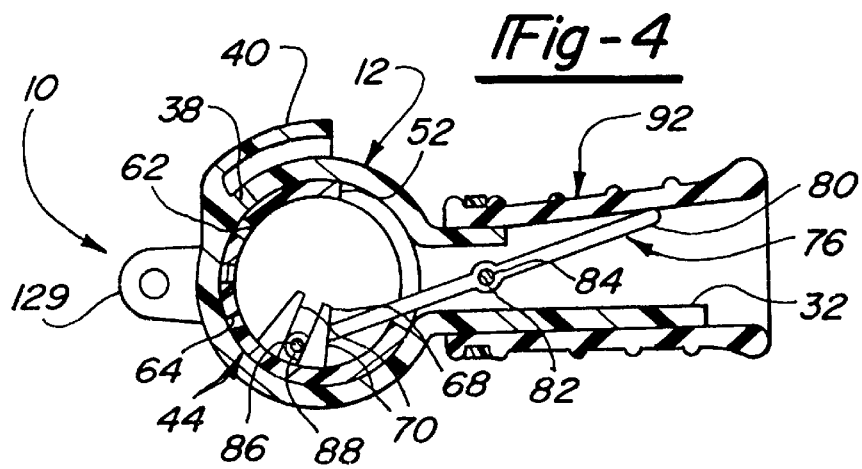
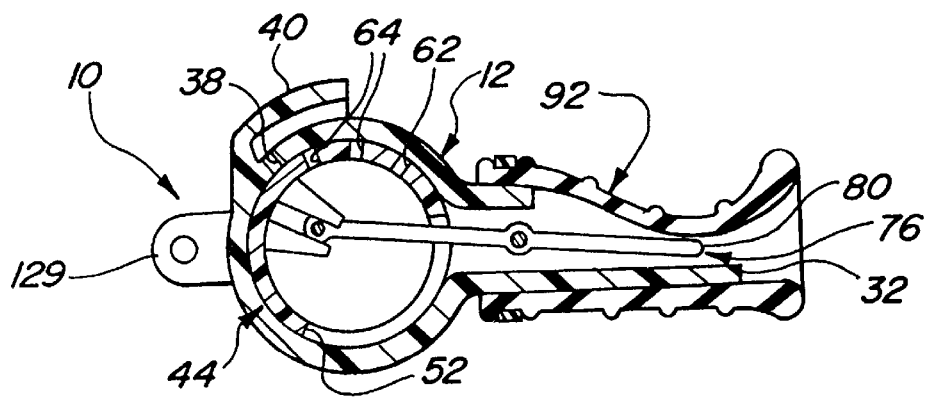

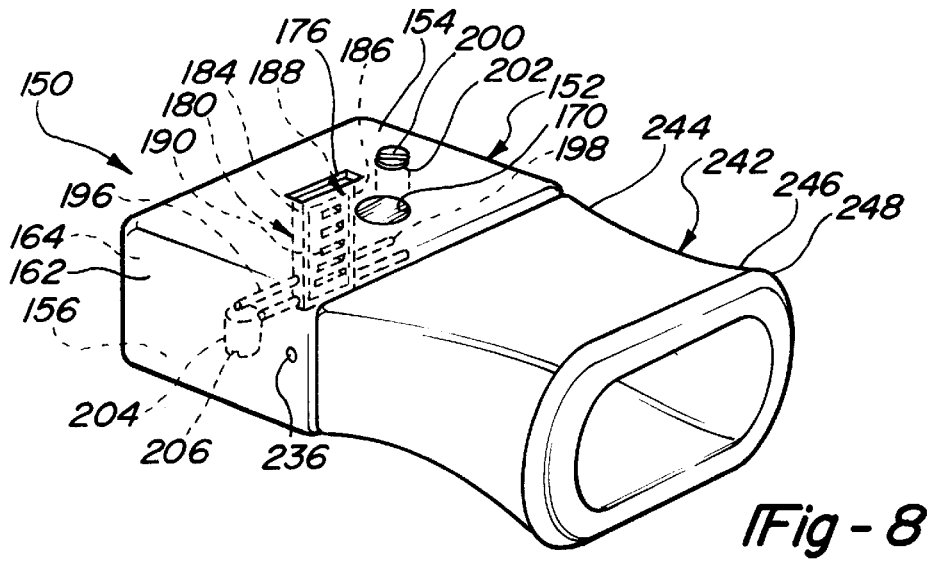
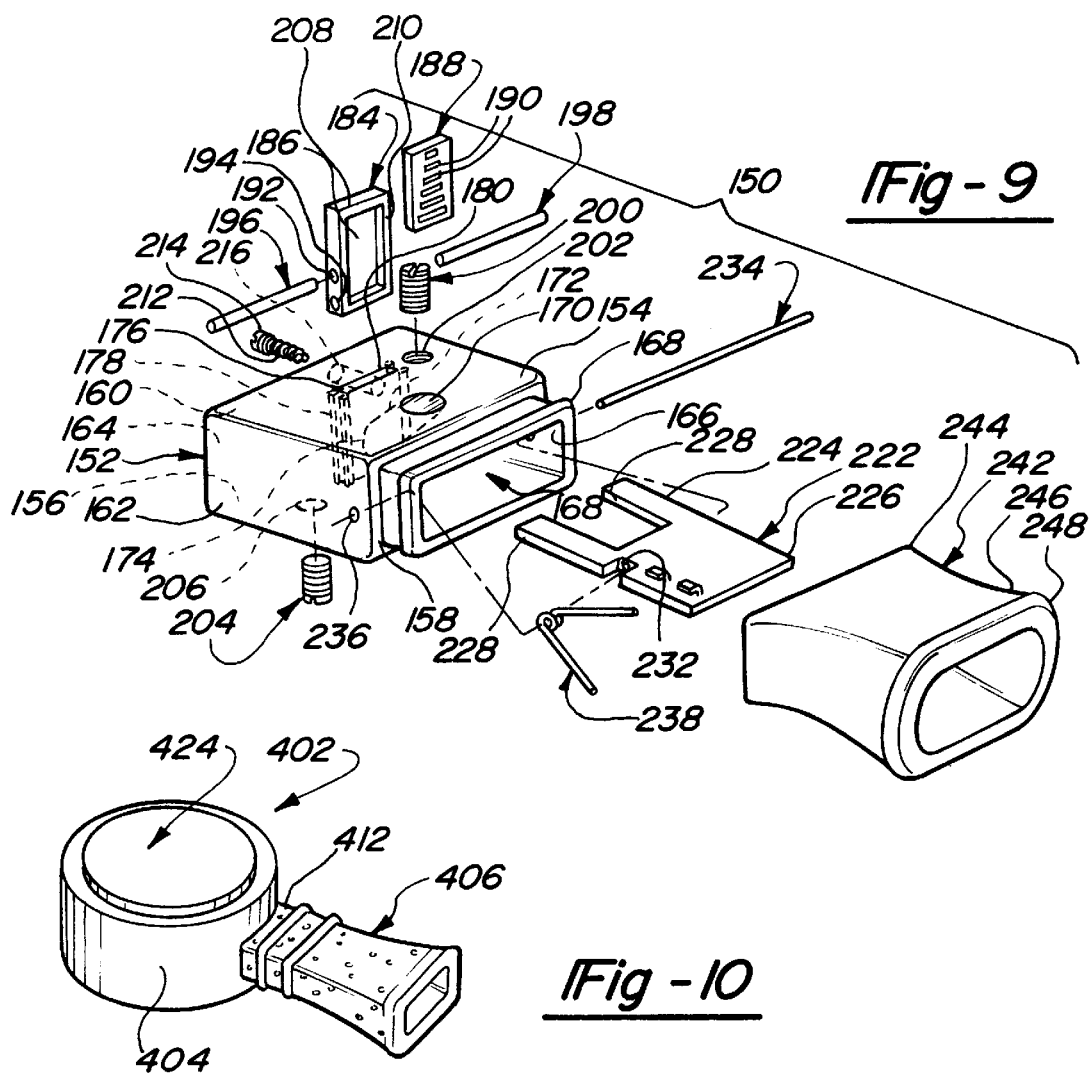

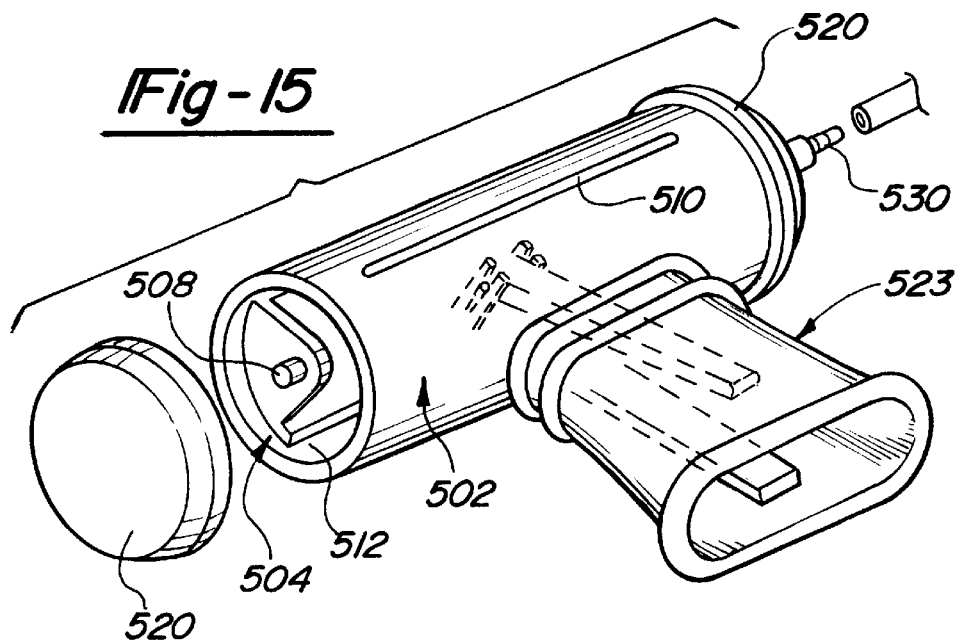
*Fig-15*
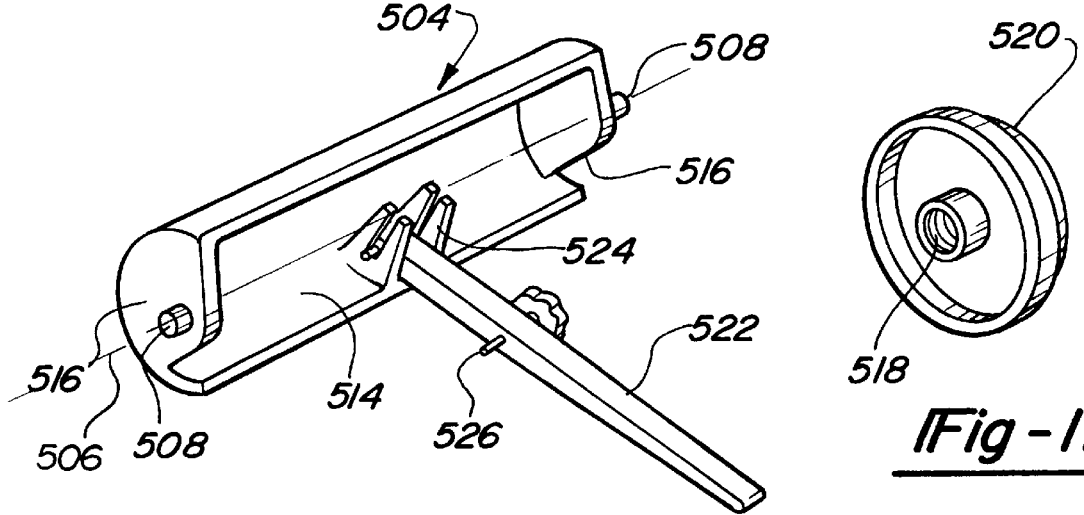
*Fig-16*
*Fig-17*

PORTABLE PERSONAL BREATHING APPARATUS

This is a continuation of application Ser. No. 08/386,375 filed on Feb. 10, 1995, now abandoned.

BACKGROUND OF THE INVENTION

The present invention relates to a portable respiratory exercise apparatus providing resistance and intra-trachea bronchial percussion on inspiration and expiration to increase pulmonary efficiency, while improving cilial movement which assists mobilization of intra-bronchial mucous or secretions within the lungs.

Research has shown that by practicing deep abdominal breathing, abdominal muscle pressure and temperature are raised, digestion and absorption of foods are improved and pulmonary efficiency is increased. In addition, taking deep breaths while performing little physical movement causes a superfluous amount of oxygen to be made available. Because the large muscular tissue is not consuming the oxygen an increased oxygen supply is made available for many other body systems, such as the brain and the heart.

Forcible and prolonged inspiration and expiration causes a greater expansion and collapse of the air vesicles (alveoli), especially those deep in the lung tissue. By providing resistance to inspiration and expiration, pulmonary muscles are strengthened and developed, thereby allowing a freer and greater exchange of oxygen and carbon dioxide. Persons suffering from lung ailments, healthy persons, and athletes can all improve their pulmonary efficiency through forcible and prolonged inspiration and expiration against resistance.

Some people are able to take only shallow breaths because they are suffering from lung ailments such as asthma, emphysema, chronic bronchitis, chronic obstructive pulmonary disease, or other ailments which reduce the oxygen/$CO_2$ exchange. Frequently, patients recovering from abdominal surgery experience pain during deep breathing and may therefore restrict their own breathing to shallow breaths. In both of the above situations, recovery is slowed because the patients suffer from reduced exchange of oxygen and carbon dioxide in the tissue. Further, the patients are at risk of developing atelectasis because their lungs are not being fully expanded. Atelectasis is a partial collapse of the lungs, possibly leading to necrosis of the lung alveoli. This exacerbates any ailments from which the patient may be suffering by causing poor oxygen exchange in the lungs and possibly resulting in pneumonia.

Patients with emphysema further suffer from mucous blockages in the lungs. Cilia, tiny hairlike structures in the lungs, become flattened down and clogged by mucous. Vibration of the air during inspiration or expiration can cause vibration of the lungs, lung passages (bronchi), and cilia of the patient. This vibration sometimes provides relief to the patient by bringing the cilia to an upright position and mobilizing the mucous, facilitating the expectoration thereof.

Known respiratory exercisers utilize a ball inside a large tube. A user exhales or inhales through a smaller attached tube, causing the ball to rise proportionally to the rate of airflow. However, these known respiratory exercisers only provide resistance to inspiration or expiration, but not both. Further, the large tube must be maintained in a vertical position in order for the respiratory exerciser to operate correctly. This is inconvenient for persons suffering from lung ailments who may be confined to bed and for athletes who wish to restrict respiratory volume flow during exercise. Still further, this respiratory exerciser does not provide a percussive effect on the user; i.e., a vibration of the air on inspiration or expiration.

Another known respiratory exerciser provides a mask which allows air to be inhaled freely and provides resistance against the expiration of air. The masks do not provide resistance to inspiration and do not provide vibration. Further, the masks are too large to be conveniently portable.

Another respiratory exerciser provides a vibration effect upon expiration. A patient exhales into a tube connected to a conical element loosely supporting a ball. When a patient exhales through the tube, the ball is displaced from the conical element causing an oscillatory movement of the ball, thereby generating a variable pressure opposing the expiration. There are several disadvantages to this device. It does not provide vibration of air during inspiration. It is inconvenient for some patients because it must be maintained at a horizontal position during use. Further, the device provides only varying oscillations in air pressure, rather than a sharp percussion of the air by rapid bursts of air pressure from complete opening and closure of the air passages.

Another respiratory exerciser provides a vibration effect upon either inspiration or expiration by using a pair of adjacent air passageways each containing a reed. Each passageway contains a valve utilizing a coil spring to allow either inspiration or expiration. The compression of each spring can be adjusted to vary the resistance to inspiration and expiration independently. As the patient inhales through one passageway and exhales through the other, air flowing past each reed causes each reed to rapidly vibrate, causing a vibration effect on the lungs of the patient. However, adjustment of the coil spring compression during inspiration and expiration is not convenient. Further, vibration of the air is not as effective as would be a sharp percussion of the air by rapid, complete opening and closure of the air passages.

SUMMARY OF THE INVENTION

The present invention provides a respiratory exercise apparatus which is portable, non-positional, and provides percussion and resistance during inspiration and expiration. The user can adjust the resistance by opening and closing the jaw muscles on a lever disposed within a mouthpiece. By opening and closing the jaw muscles during inspiration and expiration, the respiratory exercise apparatus provides a strong percussion effect which will expand the air vesicles deep in the lungs and loosen mucous blockages in the lungs. Because the present invention provides rapid intermittent complete closure of the airflow in and out of the user's lungs during percussion, a more effective percussion effect is obtained than by merely vibrating the air pressure.

In the disclosed embodiments, the respiratory exercise apparatus includes a generally cylindrical main body having at least one main aperture. Although disclosed as cylindrical, in some embodiments, the main body can be non-cylindrical. An inner cylinder is disposed within the main body and is rotatable within the main body. Upon rotation of the inner cylinder, at least one main aperture is opened and closed.

In one embodiment, the main body includes a plurality of apertures. Upon rotation of the inner cylinder, greater or fewer numbers of inner apertures align with main apertures, thereby providing a means for adjusting the resistance to inspiration and expiration. In this embodiment the respiratory exercise apparatus can function as a resistance breathing apparatus and as a percussive breathing apparatus by varying the position of the jaws. By closing the jaws slightly and holding them in place the resistance to inspiration and expiration can be changed. By opening, closing, or partially closing the apertures in the main body further, variation in resistance to inhaling and exhaling can be achieved. Additionally, by rapidly opening and closing the jaws as the user breathes in and out, percussion of the lungs can be obtained. The resistance to airflow during percussion can also be varied by opening, plugging, or partially plugging one or more apertures in the main body.

The present invention provides the user with the ability to rotate the inner cylinder, and thereby adjust the resistance, by opening and closing the jaw muscles on the mouthpiece. A lever disposed within the mouthpiece engages the inner surface of the inner cylinder. When the lever is depressed, the other end of the lever rotates the inner cylinder relative to the main body.

The present invention is also effective for providing a percussion effect upon inspiration and expiration. By rotating the inner cylinder during inspiration and expiration, the inner apertures are sequentially aligned with the main apertures. In between the alignment of the apertures, the inner cylinder closes the main apertures. This opening and closing of the main apertures provides a strong percussion effect which opens and expands air vesicles deep in the lungs, improving pulmonary efficiency. Further, patients suffering from mucous blockages can obtain relief by percussing the lungs and cilia and loosening up mucous blockages.

In another embodiment of the present invention, the breathing device is directed to percussion of the lungs. In this embodiment, the inner drum is replaced with a biased valve that can be opened and closed by biting down or releasing the mouthpiece. Again, the opening and closing provides bursts of air to the lungs for maximum percussion action.

In still another embodiment, a sector of a cylinder is rotated to open and close an elongated slot. This embodiment is directed to percussing the lungs through manipulation of the mouthpiece.

In another embodiment of the present invention, airflow volume control is achieved through the use of a manually-operated slide. This embodiment allows easy and accurate adjustment of the airflow restriction for use in inspiration and expiration or for percussion. The slide can be adjusted by the user's doctor, who could gradually increase the resistance to breathing as the user's pulmonary muscles strengthen.

Several other embodiments are illustrated. It will be apparent to one of ordinary skill that other embodiments could be used to obtain similar results and objectives and still be within the scope of the invention. With reference to the following Brief Description of the Drawings and disclosure, the invention will be described.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 3 is a top view of the apparatus shown in FIG. 1, with the percussion air deflector removed;

FIG. 4 is a sectional view taken along line 4—4 of the respiratory exercise apparatus of FIG. 3;

FIG. 5 is the respiratory exercise apparatus of FIG. 4 in which the inner cylinder has been fully rotated;

FIG. 8 is a perspective view of a further embodiment of the present invention;

FIG. 9 is an exploded perspective view of the apparatus of FIG. 8;

FIG. 10 is a perspective view of a further embodiment of the present invention.

FIG. 15 is a perspective view of a further embodiment of the present invention;

FIG. 16 is a perspective view of the interrupter used in the device of FIG. 15.

FIG. 17 is an end cap of the device of FIG. 15.

DESCRIPTION OF THE PREFERRED EMBODIMENT

Figure 1:
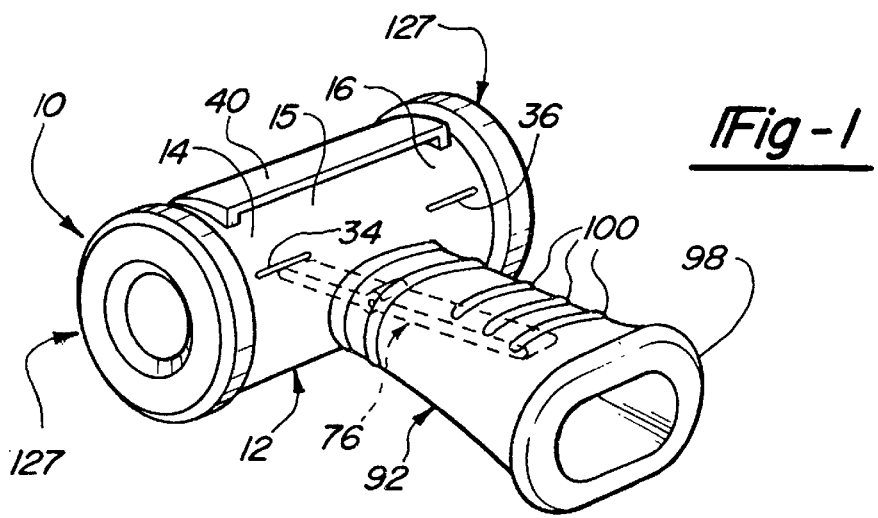
FIG. 1 is a perspective view of a respiratory exercise apparatus in accordance with the present invention.

A respiratory exercise apparatus 10 is shown in FIG. 1 in accordance with a preferred embodiment of the present invention.

Figure 2:
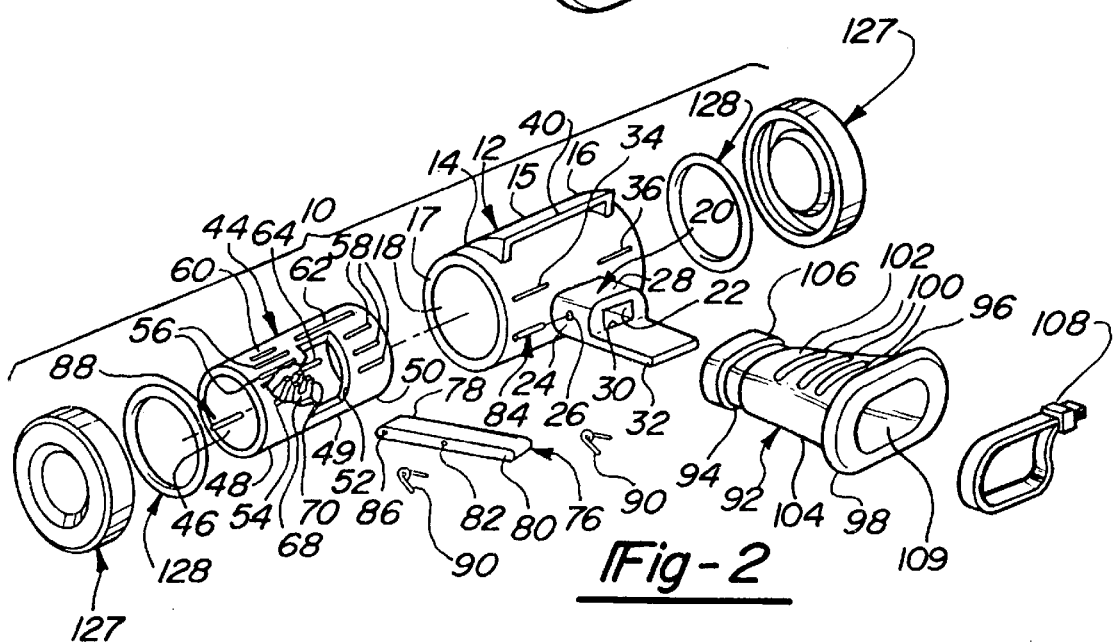
FIG. 2 is an exploded perspective view, partially broken away, of the respiratory exercise apparatus of FIG. 1.

As can be seen in FIG. 2, the respiratory exercise apparatus 10 includes a generally cylindrical main body 12 having a left section 14, a central section 15, and a right section 16. The main body 12 further includes axial ends 17 and a cylindrical cavity 18. A main body mouth 20 disposed on the central portion 15 of the main body 12 has an orifice 22 in communication with the cylindrical cavity 18. The main body mouth 20 comprises two side walls 24, each having an aperture 26. The main body mouth 20 further comprises an upper wall 28, a lower wall 30, and a tongue 32 projecting from the lower wall 30.

As can be seen in FIGS. 2 and 3, the main body 12 includes a main left aperture 34 in the left section 14 in communication with the cylindrical cavity 18. A similar main right aperture 36 is disposed in the right section 16 of the main body 12 in alignment with the main left aperture 34. Circumferentially spaced from the main left aperture 34 and the main right aperture 36, a main percussion aperture 38 extends from the central section 15 to the right section 16 in the main body 12. Preferably, the main apertures 34, 36, 38 are elongated, narrow slots. A percussion air deflector 40, shown in FIG. 2 but removed in FIG. 3, is disposed on the main body 12 over the main percussion aperture 38.

As can be seen in FIG. 2, the respiratory exercise apparatus 10 further includes a flow interrupter which, in this embodiment, is an inner cylinder 44 disposed within said main body 12 and rotatable relative to the main body 12. The inner cylinder 44 has an inner surface 46, a left section 48, a central section 49, and a right section 50. The inner cylinder 44 includes a central orifice 52 in the central section 49. In the disclosed embodiment, the central orifice 52 is rectangular. An inner inspiration aperture 54 is disposed in the left section 48 of the inner cylinder 44 adjacent the central orifice 52. Circumferentially spaced from the inner inspiration aperture 54 are three circumferentially-spaced inner apertures 56 in the left section 48 of inner cylinder 44. Each of the three inner apertures 56 has an aligned inner aperture 58 disposed on the right section 50 of inner cylinder 44. Further circumferentially spaced from the three inner apertures 56 is a slightly smaller inner expiration aperture 60 disposed on the left section 48 of the inner cylinder 44. A first inner percussion aperture 62 extends through the central section 49 to the right section 50 of inner cylinder 44 and is aligned with inner expiration aperture 60. Two identical inner percussion apertures 64 are spaced circumferentially from the first inner percussion aperture 62.

In order to provide a sharp, rapid opening and closure of the airflow through the cylindrical cavity 18, all of the inner apertures and main apertures are generally narrow slots elongated axially with respect to the main body 12 and inner cylinder 44. In the preferred embodiment, the main apertures 34, 36, and 38 are elongated, narrow slots. They are narrow so the air pressure immediately drops. The slightly wider slot 38 in the outer body is wide enough so as to get a maximum drop in pressure. The width of the slot 38 in the main body should be wide enough to get a maximum drop in pressure. The land between the slots on the inner cylinder should be wide enough to allow pressure to build up to a maximum amount.

A yoke 68 is mounted on the inner surface 46 of the inner cylinder 44 in the central section 49 opposite the central orifice 52. The yoke 68 comprises two circumferentially-spaced pair of axially-spaced guides 70.

A lever 76 has an inner end 78, an outer end 80 and a central aperture 82 disposed between the inner end 78 and the outer end 80. The inner end 78 is disposed within the main body mouth 20 of main body 12. A pivot pin 84 is inserted through the apertures 26 in the side walls 24 of the main body mouth 20 and through the central aperture 82 in lever 76. An aperture 86 at the inner end 78 of the lever 76 retains a pin 88 in engagement with the yoke 68. Biasing means, such as a pair of springs 90 coiled about the pivot pin 84, bias the end 80 of the lever 76 away from the tongue 32 of the main body mouth 20.

Figure 2A:
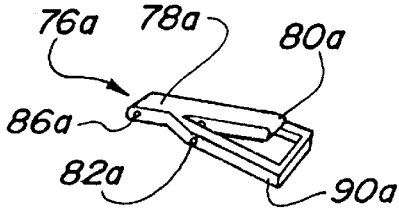
FIG. 2A is a perspective view of an alternative lever having integrated biasing means.

An alternate lever 76a having integrated biasing means 90a is shown in FIG. 2A. The lever 76a has an inner end 78a and an outer end 80a. The lever 76a is formed integrally with a biasing member 90a which projects from the lever 76a and forms an acute angle with the outer end 80a. A central aperture 82a through the lever 76a, including the biasing member 90a, is disposed between the inner end 78a and outer end 80a. The biasing member 90a biases the outer end 80a of the lever 76a away from the tongue 32 on the main body 12. An aperture 86a retains a pin 88 in engagement with yoke 68.

A tubular rubber mouthpiece 92, generally oblong in transverse section, has an inner end 94 and an outer end 96. An outer flange 98 is disposed at the outer end 96. A plurality of ribs 100 project from the upper surface 102 and the lower surface 104 of the mouthpiece 92. A pair of axially-spaced inner flanges 106 are disposed about the circumference of the inner end 94. The main body mouth 20 of the main body 12 is inserted into the inner end 94 of the mouthpiece 92. A band 108 or other removable securing means is tightened around the inner end 94 of mouthpiece 92 between the inner flanges 106. The outer end 80 of the lever 76 is disposed within the mouthpiece 92. The mouthpiece 92 can be used to bias the outer end 80 of the lever 76 as an alternative to the springs 90 by securing the outer end 80 of the lever 76 to the upper inner surface 109 of the mouthpiece 92 with an adhesive (not shown) or a pocket (not shown) formed on the upper inner surface 109 of the mouthpiece 92.

Figure 2B:
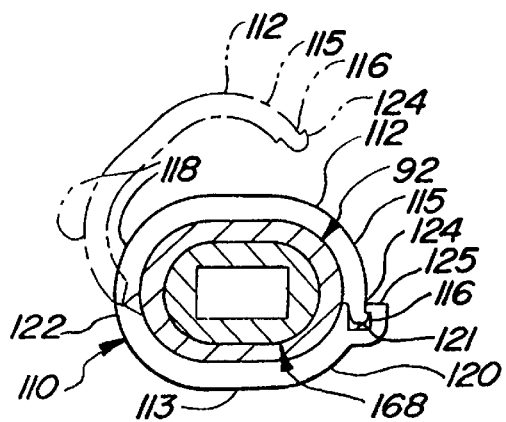
FIG. 2B illustrates an alternate band which includes upper and lower u-shaped numbers.

An alternate band 110, shown in FIG. 2B includes an upper U-shaped member 112 and a lower U-shaped member 113. The upper U-shaped member 112 includes an upper right arm 115 having a head portion 116 and an upper left arm 118. The lower U-shaped member 113 includes a lower right arm 120 having a pocket 121 and a lower left arm 122. The lower left arm 122 and the upper left arm 118 are hingeably connected. To secure the band 110 over the mouthpiece 92, the head portion 116 of the upper right arm 115 is inserted into the pocket 121 of the lower right arm 120, where complementary clasp portions 124, 125 interlock.

A pair of end caps 127 are removably secured to the axial ends 17 of the main body 12. A rubber ring 128 between each end cap 127 and axial end 17 provides a substantially airtight seal between the end caps 127 and the main body 12. An eyelet 129 is disposed on the main body 12 opposite the main body mouth 20. The eyelet 129 permits a chain or cord to be attached so that the apparatus 10 can be hung around a user's neck for convenience.

In operation, the user holds the respiratory exercise apparatus 10 with the mouth over the outer flange 98 of the mouthpiece 92. The user can open or close the jaw muscles on the mouthpiece 92, moving the outer end 80 of the lever 76 toward the tongue 32 on main body 12. The lever 76 pivots on pivot pin 84, causing the inner end 78 of the lever 76 to raise the yoke 68 and rotate the inner cylinder 44 within the cylindrical cavity 18 of the main body 12.

In this manner, the user can control the rotation of the inner cylinder 44 relative to the main body 12. As can be seen in FIGS. 4–5, the user can align different apertures on the inner cylinder 44 with the main left aperture 34, main right aperture 36, and main percussion aperture 38. It should be apparent that the present invention need not be maintained at a horizontal position.

During inspiration, the jaw muscles are naturally relaxed, allowing the apparatus to reach the initial position with the lever 76 up. With the lever 76 up, only the inner inspiration aperture 54 and the main left aperture 34 are aligned. This provides the greatest restriction to airflow volume during inspiration.

By subsequently closing or partially closing the jaw muscles on the mouthpiece 92, the user can reduce the restriction to airflow during expiration. As the user presses the lever 76 downward and the inner cylinder 44 begins to rotate relative to the main body 12, the three inner apertures 56 in the left section 48 are sequentially aligned with the main left aperture 34 simultaneous to the alignment of each of the three inner apertures 58 in the right section 50 with the main right aperture 36 and simultaneous to the alignment of each of the three inner percussion apertures 62, 64 with the main percussion aperture 38. When three inner apertures are simultaneously aligned with main apertures, the least airflow restriction is offered to expiration. Finally, with the lever 76 fully depressed to the tongue 32, the inner expiration aperture 60 is aligned with the main left aperture 34 while the right portion of the first inner percussion aperture 62 is aligned with the main right aperture 36. In this position, expiration is provided with a medium amount of resistance by the closure of the main percussion aperture 38 and opening of the main left aperture 34 and the main right aperture 36.

When the user relaxes the jaw muscles and allows the spring 90 to raise the outer end 80 of the lever 76, the inner cylinder 44 is rotated back to the initial position.

At different rotational positions of the inner cylinder 44, greater or fewer apertures of greater or lesser size will align, offering a wide range of resistance to inspiration and expiration selectable by merely opening or closing the jaw muscles. The user can easily select one position during inspiration and rotate the inner cylinder 44 to another position during expiration. Further, the user can plug either or both of the main left aperture 34 and main right aperture 36 for additional adjustment of resistance. During expiration, positive feedback is provided to the user in the form of air blowing gently on the user's face from the percussion air deflector 40. Additionally, the exercise apparatus makes a distinct sound as the air is inhaled and exhaled. This provides the user with an auditory indicator of the effort being expended. Both of these indicators provide an incentive to the user. The indicators also provide an indication and incentive to fully empty and fill the lungs during use. This indication ability is an attribute of each of the disclosed embodiments.

It should be apparent that the present invention could alternatively be used to adjust the resistance to inspiration as well as expiration, and that an inner cylinder having different sizes of apertures or different numbers of apertures could be tailored to the user's individual needs.

For percussion effect, the user rapidly and repeatedly opens and closes the jaw muscles during inspiration and expiration. As can be seen in FIGS. 4–5, the large inner percussion apertures 62, 64 are sequentially aligned with the main percussion aperture 38 during rotation, providing intermittent bursts of air pressure changes. In between the percussion apertures 38, the inner cylinder 44 closes the apertures 34, 36, and 38. This provides a strong percussion effect to the lungs of the user during both inspiration and expiration which will help fully expand the air vesicles deep in the lungs, thereby increasing pulmonary efficiency. In a user with mucous blockages in the lungs, the intermittent closure of the apertures in the respiratory exercise apparatus 10 provides a strong percussion effect which unclogs the cilia in the lungs and mobilizes the mucous. Again, the user can plug either or both of the main left aperture 34 and main right aperture 36 for adjustment of resistance and percussion. Alternatively, the user can open and close the jaw muscles slowly during expiration and inspiration, thereby allowing air pressure to build within the lungs each time the inner cylinder 44 closes the apertures 34, 36, 38 in the main body 12.

The speed or rapidity of opening and closing of the jaws with a given amount of pulmonary exertion, along with the flow or duration of the air, determines the amount of percussion. Percussion can be elevated by a slight hesitation with the jaw muscles either opened or closed. Also, either the hesitation or the rapidity of opening and closing of the jaw muscles allows the patient to voluntarily control the length of inspiration or expiration.

The respiratory exercise apparatus 10 is compact, conveniently portable, and can be carried in a pocket or purse. It can be worn on a chain through the eyelet 129 on the main body 12. The mouthpiece 92 and inner cylinder 44 can be removed by the user to facilitate cleaning. In addition, the user can substitute an inner cylinder having different arrangements of apertures for the inner cylinder 44. A user could substitute inner cylinders of gradually increasing resistance or an inner cylinder recommended by a doctor.

Figure 6:
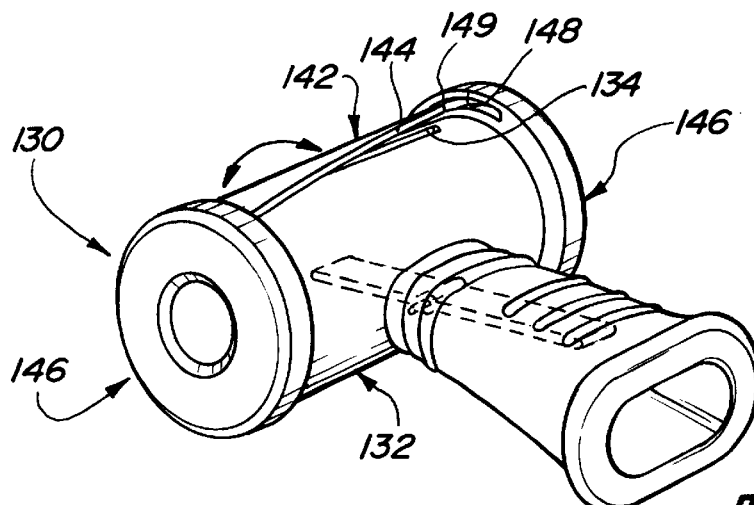
FIG. 6 is a perspective view of a respiratory exercise apparatus in accordance with another embodiment of the present invention.
Figure 7:
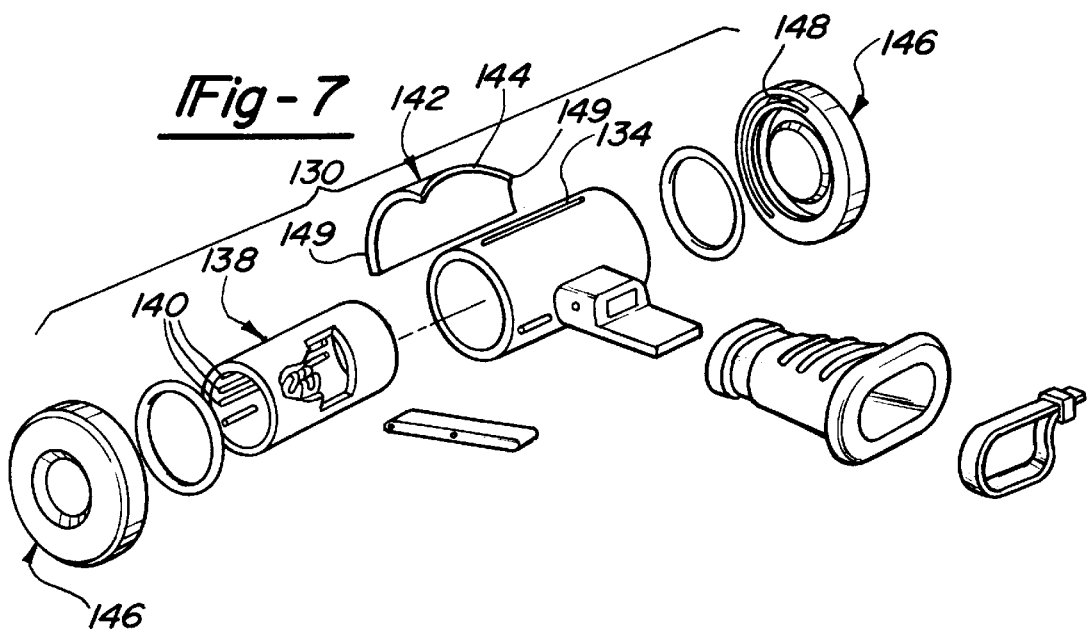
FIG. 7 is an exploded perspective view of the respiratory exercise apparatus of FIG. 6.

In another embodiment of the present invention, shown in FIGS. 6–7, a respiratory exercise apparatus 130 includes a main body 132 having a single elongated main percussion aperture 134. An inner cylinder 138 has a plurality of elongated, circumferentially-spaced inner percussion apertures 140 which are sequentially aligned with the main percussion aperture 134 upon rotation of the inner cylinder 138 relative to the main body 132.

In this embodiment, an adjustment slide 142 is disposed on the main body 132 over the main percussion aperture 134. The adjustment slide 142 is curved and has a tapered leading edge 144. Two end caps 146 each having a diameter greater than the diameter of the main body 132 are removably secured to the axial ends of the main body 132. Each end cap 146 provides a peripheral channel 148 around approximately half the circumference of the main body 132 and end caps 146. Two axial ends 139 of the adjustment slide 142 are slidably received within the channels 148 in the end caps 146.

In operation, the user can adjust the resistance and percussion effect by manually moving the adjustment slide 142 to cover a selected portion of the main percussion aperture 134 with the tapered leading edge 144. The user rotates the inner cylinder 138 within the main body 132 by opening and closing the jaw muscles. When each inner percussion aperture 140 is aligned with the main percussion aperture 134, air can flow in or out of the lungs. Between the inner percussion apertures 140 the inner cylinder 138 will cover the main percussion aperture 134, interrupting the flow of air. By opening and closing the jaw muscles and rotating the inner cylinder 138 during inspiration and expiration, the user can achieve a percussion effect as each of the inner percussion apertures 140 is sequentially aligned with the main percussion aperture 134.

In another embodiment of the present invention shown in FIGS. 8 and 9, a respiratory exercise apparatus 150 includes a main body 152 having an upper wall 154, a lower wall 156, a front wall 158, a rear wall 160 and two side walls 162 defining an inner cavity 164. An orifice 166 in the front wall 158 is in communication with the inner cavity 164. A main body mouth 168 projects outwardly from the main body 152 around the periphery of the orifice 166. A respiration aperture 170 in the upper wall 154 is in communication with the inner cavity 164 by means of a shaft 172 extending downward and rearward and terminating at an inner end 174 which is perpendicular to the upper and lower walls 154, 156 and below a rectangular orifice 176 in the upper wall 154. Guide rails 178 on either side of the rectangular orifice 176 extend between the upper wall 154 and the lower wall 156 thereby defining a channel 180.

A sliding plate 184 having an opening 186 adapted to snap fit an insert 188 is slidably disposed within the channel 180. An insert 188 having a plurality of horizontally-elongated vertically-spaced apertures 190, preferably of different sizes, is received within the opening 186 in the sliding plate 184. A pair of vertically spaced horizontal apertures 192, 194 are disposed in the sliding plate 184 behind the insert 188. A lower limit stop 196 is inserted through the upper aperture 192. An upper limit stop 198 is inserted through the lower aperture 194. The lower limit stop 196 extends toward the left side of the main body 152 further than the upper limit stop 198 while the upper limit stop 198 extends to the right of the main body 152 further than the lower limit stop 196. An upper screw 200 is threaded through an aperture 202 to the right of the rectangular orifice 176 in the upper wall 154 of the main body 152. A lower screw 204 is threaded through an aperture 206 on the left side of the channel 180 in the lower wall 156.

A series of vertically spaced detents 208 are disposed on the right side of the rear surface 210 of the sliding plate 184. A spring 212 and plunger 214 are inserted through an aperture 216 in the rear wall 160 of the main body 152. The spring 212 biases the plunger 214 to engage the detents 208 in the sliding plate 184.

A lever 222 has an inner end 224 and an outer end 226. The inner end 224 comprises a left arm 228 and a right arm 230. The left arm 228 is disposed between the upper limit stop 198 and lower limit stop 196 on the left side of the sliding plate 184. The right arm 230 is disposed between the upper limit stop 198 and lower limit stop 196 on the right side of the sliding plate 184. The lever 222 further includes a central aperture 232 between the inner end 224 and the outer end 226. A pivot pin 234 is inserted through a pair of apertures 236 in the side walls 162 and through the central aperture 232 in the lever 222. A spring 238 or other biasing means is disposed on the pivot pin 234 to bias the outer end 226 of lever 222, as described above.

A rubber mouthpiece 242 has an inner end 244 and an outer end 246. The inner end 244 is disposed about the main body mouth 168. An outer flange 248 is disposed about the circumference of the outer end 246.

In operation, the user holds the respiratory exercise apparatus 150 with the mouth over the outer flange 248 of the mouthpiece 242. The user can open or close the jaw muscles on the mouthpiece 242 moving the outer end 226 of the lever 222 downward. The lever 222 pivots on pivot pin 234 causing the inner end to raise the sliding plate 184 by engaging the lower limit stop 196. As the sliding plate 184 is raised, the spring 212 biases the plunger 214 to engage the detents 208 on the rear surface 210 of the sliding plate 184, thereby causing the sliding plate 184 to move in discrete increments, sequentially aligning each of the apertures 190 with the inner end 174 of the shaft 172. As the user relaxes the jaw muscles, the spring 238 biases the outer end 226 of the lever 222 upward moving the outer end 226 of the lever 222 and the sliding plate 184 downward.

In this manner, the user can control the position of the sliding plate 184 relative to the inner end 174 of the shaft 172. The user can align different apertures on the sliding plate 184 with the inner end 174 of the shaft 172. Again, it should be apparent that the present invention need not be maintained at a horizontal position.

During inspiration, the jaw muscles are naturally relaxed allowing the apparatus to reach the initial position with the lever 222 up. Using the insert 188 shown in the figure, with the lever 222 up, only the uppermost aperture 190 of the insert 188 is aligned with the shaft 172. The insert 188 shown would provide the greatest restriction to air flow volume during inspiration.

By subsequently closing or partially closing the jaw muscles on the mouthpiece 242, the user can reduce the restriction to airflow during expiration. As the user presses the lever 222 downward, the sliding plate 184 is raised in discreet increments as each of the apertures 190 is sequentially aligned with the inner end 174 of the shaft 172. Using the insert 188 shown, the least restriction to expiration is provided with the outer end 226 of the lever 222 fully depressed, aligning the lowermost aperture 190 of the insert 188 with the shaft 172.

When the user relaxes the jaw muscles and allows the spring 238 to raise the outer end 226 of the lever 222, the sliding plate 184 is returned to the initial position.

It should be apparent that the present invention could alternatively be used to adjust the resistance to inspiration as well as expiration. Further, because the insert 188 is snap fit into the opening 186 of sliding plate 184, different inserts having increasing or decreasing size apertures could be selected to for the individual user's needs.

For percussion effect, the user rapidly opens and closes the jaw muscles during inspiration and expiration. The apertures 190 are sequentially aligned with the inner end 174 of the shaft 172 providing intermittent bursts of air pressure changes. In between the apertures 190 the sliding plate 184 closes the shaft 172. This provides a strong percussion effect to the lungs of the user during both inspiration and expiration which will help fully expand the air vesicles deep in the lungs, thereby increasing pulmonary efficiency. In a user with mucous blockages in the lungs, the intermittent closure of the apertures in the respiratory exercise apparatus 150 provides a strong percussion effect which unclogs the cilia in the lungs and mobilizes the mucous. Alternatively, the user can open and close the jaw muscles slowly during expiration and inspiration, thereby allowing air pressure to build within the lungs each time the apertures 190 in the sliding plate 184 close the shaft 172.

Figure 11:
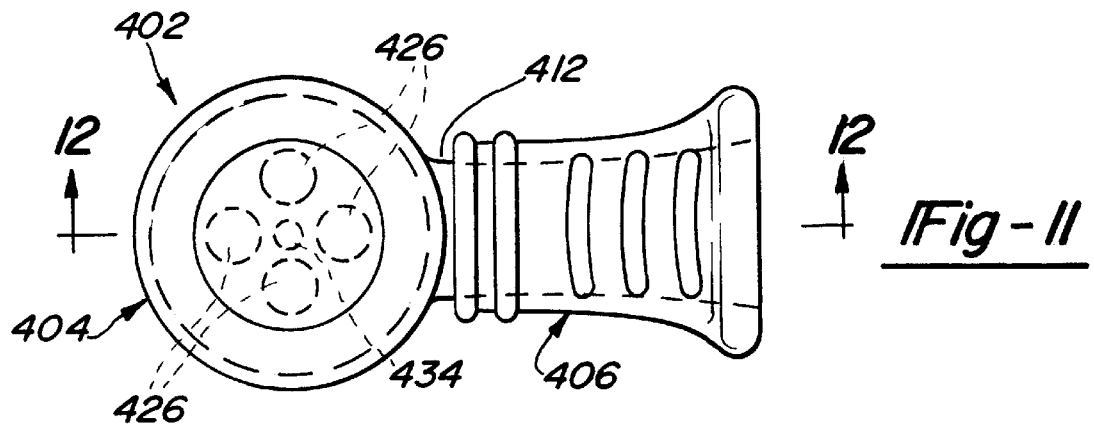
FIG. 11 is a top view of a still further embodiment of the present invention.

With reference to FIG. 10, a further embodiment of the present invention is shown generally at 402. In this embodiment, the breathing apparatus has a body portion 404, which is illustrated as being cylindrical; however, it could take other shapes, including square, triangular, polygonal, etc. A mouthpiece 406 is interconnected to the body portion 404 and is in communication with a cavity 408 within body portion 404. In the disclosed embodiment, there is an elongated support 410, which extends into the mouthpiece 406 to support one side of the mouthpiece. See FIG. 11. In the preferred embodiment, the mouthpiece 406 is made of a pliable rubber material. In the disclosed embodiment, the body portion 404 includes a mounting flange 412 for mounting mouthpiece 406 upon body portion 404. The support 410 is illustrated as being an extension of mounting flange 412.

Figure 12:
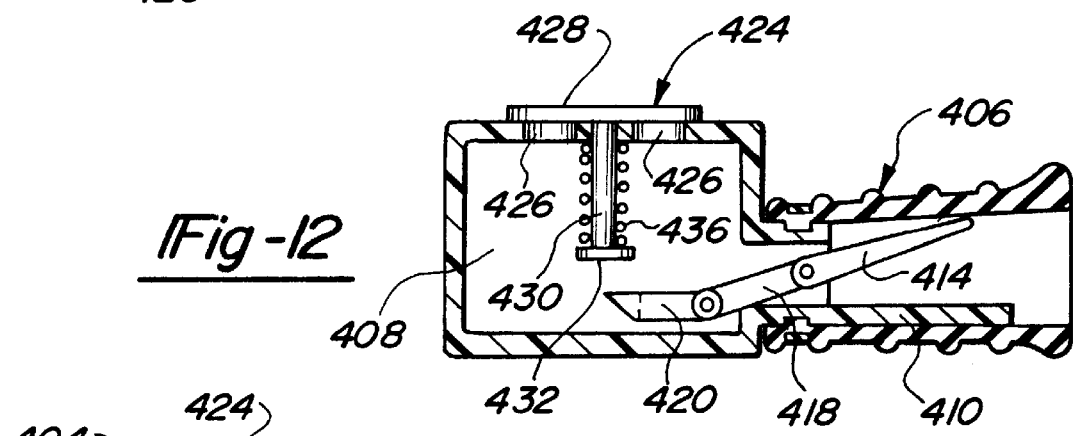
FIG. 12 is a cutaway side view of FIG. 10 with the valve closed and the mouthpiece open.
Figure 13:
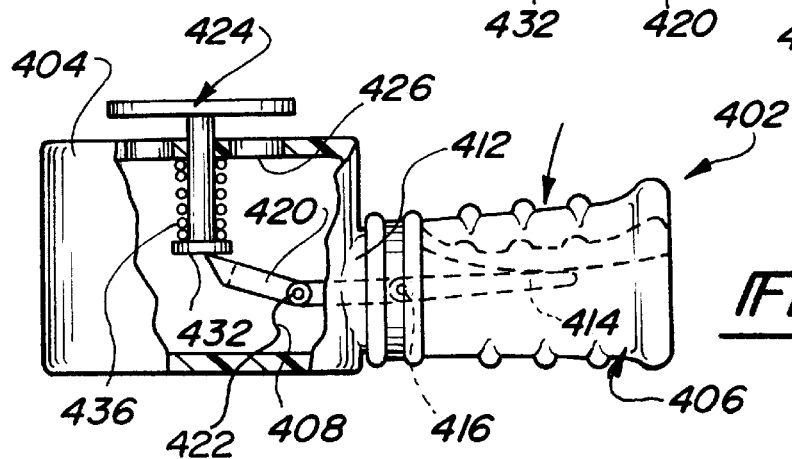
FIG. 13 is a cutaway side view of FIG. 10 with the valve open and the mouthpiece partially closed.
Figure 14:
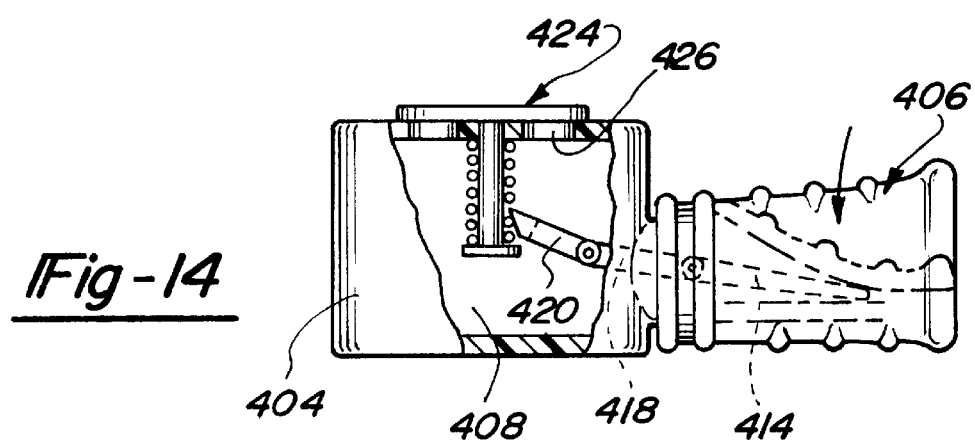
FIG. 14 is a cutaway side view of FIG. 10 with the valve closed and the mouthpiece partially closed.

A control lever 414 is pivotally mounted within body portion 404 and extends between mouthpiece 406 and cavity 408. The control lever is mounted upon a pivot pin 416 so that it can be pivoted between the positions illustrated in FIGS. 11–13. The disclosed control lever 414 is an articulated member having an arm 418 and an arm 420. The two arms are pivotally mounted at 422, with arm 420 being pivotal with respect to arm 418 in one direction but not pivotal with respect to arm 418 in the opposite direction. With reference to FIGS. 12–14, it can be seen that control lever 414 is adapted to engage a valve 424, which opens and closes apertures 426 in body portion 404. In the disclosed embodiment, there are four apertures 426; however, one or more apertures would be adequate.

The lever 414 is adapted to engage valve 424 and raise it as shown in FIG. 13 to allow the ingress of air into cavity 408 and mouthpiece 406. The lever pivots due to the user biting down on the mouthpiece 406. As the user continues to bite down on mouthpiece 406, the control lever 414 slips past valve 424, as shown in FIG. 14, allowing valve 424 to rapidly close apertures 426. Rapid closing of aperture 426 abruptly stops air flow to the lungs. When the user releases the pressure upon the mouthpiece 406, the arm 420 pivots with respect to arm 418, allowing lever 414 to return to the position shown in FIG. 11. In this way, the user can rapidly open and close his mouth upon mouthpiece 406 to permit bursts of air to percuss the user's lungs. It should be understood that the specific sequence shown in FIGS. 12–14 would not necessarily be the sequence used by a user. For example, the user could open and close the mouthpiece 406 to pivot lever 414 between the positions shown at FIGS. 12 and 13 to obtain a percussive action on the lungs.

The valve 424 is illustrated having a top flange 428, a stem 430, and a base 432. The flange 428 is adapted to close apertures 426 or to open apertures 426, depending upon the pressure placed on mouthpiece 406. The stem 430 is received within an opening 434 in body portion 404. This opening can be seen in FIG. 11. The valve is biased to the closed position. In the disclosed embodiment, a spring 436, preferably a coil spring, is positioned between the base 432 and the inner wall of body portion 404. The spring normally biases the valve to the closed position, and the bias of the spring must be overcome by lever 414 in order to open apertures 426.

With reference to FIGS. 15 through 17, a further embodiment of the present invention is shown. Briefly, in this embodiment, the main body 502 has been elongated, a segment 504 is used as a flow interrupter instead of a cylinder, as was previously disclosed in the other embodiments (it should be understood that a segment could be used in the other embodiments in place of the disclosed cylinder and a cylinder could be used in this embodiment if preferred), and the flow interrupter is mounted on a lateral axis 506 defined in the disclosed embodiment by opposed pins 508.

The elongated body 502 has an elongated, longitudinally extending slot 510. This slot is longer than the slots used in the previous embodiments and is somewhat narrower. Elongated slot 510 provides greater percussive benefit to the user. The slot 510 can be more rapidly opened and closed than a wider slot, but because of its length, it still permits a sufficient volume of air to enter and exit the interior cavity 512. As a result, the percussion effect approximates more of a vibratory action. As the user inhales, the slot 510 is open for very short periods, allowing in short, explosive bursts of air. As the user exhales, the flow of air out of the interior cavity 512 is blocked and opened rapidly, again vibrating the lungs and providing the beneficial percussive effect upon the lungs.

With reference to FIG. 16, the segment 504 is generally illustrated. As discussed above, instead of using a complete cylinder, a segment of a cylinder is used as the flow interrupter. Segment 504 includes a body portion 514 and upstanding end members 516. Pins 508 are mounted in end portions 516 and are then journaled within a bearing surface 518 formed in end caps 520. The bearing surface 518 is illustrated as being a protruding cup formed at approximately the center of end cap 520. As should be appreciated by one of ordinary skill in the art, the pins 508 are journaled in the bearing surfaces 518 of each end cap 520 to permit the segment 504 to freely rotate within body portion 502.

As in the previous embodiments, a link 522 interconnects the segment 504 with the mouthpiece 523. As previously disclosed, the link 522 is pinned to a yoke 524 extending outwardly from segment 504. The approximate mid-portion of link 522 is journaled about a pin 526, allowing the link to rock about pin 526. The opposite end of the link is positioned within mouthpiece 523, so that when the user bites down on the mouthpiece, the link rocks about pin 526, rotating segment 504 within cylinder body 502. As in the previous embodiments, the link 522 could be spring biased to return to its normal position or it could be interconnected to mouthpiece 523 so that the natural bias of mouthpiece 523 returns link 522 to its normal position.

With reference to FIG. 15, a modified end cap is illustrated, having a connector 530 integrally formed on end cap 520. This connector 530 is adapted to be interconnected to an oxygen line so that a user needing oxygen in addition to percussive effects of the lungs can receive both benefits. In use, an oxygen line would be interconnected to connector 530 to provide a flow of oxygen into body 502 through mouthpiece 523 to the user.

It should be understood by those of ordinary skill in the art that the unit depicted in FIGS. 15 through 17 could have a non-cylindrical shape. For example, the elongated body portion 502 could be rectangular in shape and employ at flat segment with pins which ride within grooves formed in the end caps. In this way, the unit could slide up and down the wall of the body portion 502 to restrict the ingress and egress of air into and out of the cavity. Furthermore, the breathing apparatus could employ relatively sliding members, as well. The inner and outer members could slide with respect to one another instead of rotating.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A respiratory exercise apparatus comprising:
   a main body having a generally cylindrical inner cavity and a main aperture;
   a mouthpiece operatively coupled to said main body;
   an inner cylinder disposed within said inner cavity of said main body and rotatable relative to said main body, said inner cylinder having at least one inner aperture, said inner cylinder being rotable relative to said main body to selectively align said at least one inner aperture with said main aperture; and
   a lever having an inner end and an outer end, said inner end of said lever engaging in inner surface of said inner cylinder, said outer end of said lever being disposed within said mouthpiece.

2. The respiratory exercise apparatus according to claim 1, further including an orifice in said inner cylinder, said mouthpiece being in communication with said orifice.

3. The respiratory exercise apparatus according to claim 2, wherein said mouthpiece extends generally radially from said generally cylindrical inner cavity of said main body.

4. The respiratory exercise apparatus according to claim 1, wherein said inner cylinder has a plurality of circumferentially-spaced inner apertures, said inner cylinder being rotatable relative to said main body to sequentially align each of said plurality of inner apertures with said main aperture.

5. The respiratory exercise apparatus according to claim 4, wherein said inner apertures and said main aperture are elongated, narrow slots.

6. The respiratory exercise apparatus according to claim 1, wherein said lever is coupled to said cylinder for rotating said inner relative to said main body.

7. The respiratory exercise apparatus according to claim 1, further including end caps removably secured to axial of said main body.

8. The respiratory exercise apparatus according to claim 1, further including an adjustment slide, slidably disposed over said main aperture on said main body.

9. The respiratory exercise apparatus according to claim 8, wherein said adjustment slide is generally curved and has a tapered leading edge.

10. A respirator exercise apparatus comprising:
   a main body having an inner cavity, a main aperture allowing the ingress and egress of air to and from said inner cavity, and an orifice adapted to allow a user to breathe air in and out of said inner cavity;
   a mouthpiece in communication with said orifice;
   means for alternately opening and closing said main aperture in said main body to selectively restrict the airflow through said inner cavity, said means being operable by manipulation of said mouthpiece, said means for alternately opening and closing said main aperture including an inner cylinder having a series of circumferentially spaced inner apertures, said inner cylinder being rotatable relative to said main body to sequentially align each of said inner apertures with said main aperture in said main body; and
   a lever having an inner end and an outer end, said inner end of said lever engaging in inner surface of said inner cylinder, said outer end of said lever disposed within said mouthpiece.

11. The respiratory exercise apparatus according to claim 10, wherein said apertures in said inner cylinder and said main aperture are elongated, narrow slots.

12. The respiratory exercise apparatus of claim 10, wherein said inner cylinder is a partial segment of a cylinder and end walls.

13. The respiratory exercise apparatus of claim 12, further including pins extending from said end walls, said pins being within said end caps.

14. The respiratory exercise apparatus of claim 13, wherein said pins are journaled within said end caps, whereby said inner cylinder can rotate within said inner cavity as a result of movement of said lever.

15. A respiratory exercise apparatus for providing resistance to inspiration and expiration comprising:
   a main body having an inner cavity, a main aperture allowing the ingress and egress of air to and from said inner cavity, and an orifice adapted to allow a user to breathe air in and out of said inner cavity;
   a restrictor for adjusting the resistance, said restrictor including an inner cylinder having a series of circumferentially spaced inner apertures, said inner cylinder being rotatable relative to said main body to align each of said inner apertures with said main aperture in said main body; and
   a lever having an inner end and an outer end, said inner end of said lever engaging said restrictor, said outer end of said lever being disposed within said orifice; said lever controlling the movement of said restrictor with respect to said main aperture to vary the resistance.

16. The respiratory exercise apparatus according to claim 15, wherein said apertures for adjusting resistance and said main aperture are elongated, narrow slots.

17. A respiratory exercise apparatus comprising:
   a main body having an inner cavity, a main aperture in communication with said inner cavity, and a mouthpiece in communication with said inner cavity;
   a movable member movably mounted to said main body, said movable member being mounted to move with respect to said main aperture to selectively open and close said main aperture in said main body; and
   a lever having an inner end and an outer end, said inner end of said lever engaging said movable member, said outer end of said lever being disposed within said mouthpiece.

18. The respiratory exercise apparatus according to claim 17, wherein said movable member includes a plurality of apertures, said plurality of apertures being of varying sizes.

19. The respiratory exercise apparatus according to claim 18, wherein said apertures in said movable member and said main aperture are elongated, narrow slots.

20. The respiratory exercise apparatus of claim 17 wherein said movable member is a valve.

21. The respiratory exercise apparatus of claim 20 wherein said valve is spring biased to normally close said main aperture.

22. The respiratory exercise apparatus of claim 21, wherein said lever extends from said mouthpiece into said main body, said lever engaging said valve and being operable to open and close said valve by manipulation of said mouthpiece.

23. The respiratory exercise apparatus of claim 22, wherein said lever includes two articulated arms, one of said arms being pivotal in one direction with respect to the other arm, said arms being fixed with respect to one another as said lever moves from the first position to the second position corresponding to said valve moving between a fully closed position and a fully open position, said lever being disengaged from said valve when said valve is fully opened; and
   said one arm pivoting with respect to said other arm as said lever is returned to the first position from the second position.

24. The respiratory exercise apparatus of claim 20, wherein said valve includes a flange for covering said main aperture, a stem extending from said flange into said main body, a base on said stem, and a spring mounted between said base and said main body to normally bias said flange against said aperture.

25. The respiratory exercise apparatus of claim 17, wherein said moveable member is a flow restrictor having a body portion defined by a partial segment of a cylinder and end walls, said lever operatively connects said flow restrictor with said mouthpiece.

26. The respiratory exercise apparatus of claim 25, further including pins extending from said end walls, said pins being mounted within a pair of end caps.

27. The respiratory exercise apparatus of claim 26, wherein said pins are journaled within said end caps, whereby said flow restrictor can rotate within said inner cavity as a result of movement of said lever.

28. A method for exercising the lungs of a user, said method comprising the steps of:
   providing a mouth adjustable exercising apparatus, said apparatus having a mouthpiece interconnected to a body portion with said body portion having at least one aperture for the ingress and egress of air through said body portion and said mouthpiece, and an adjustable air restriction means positioned adjacent said at least one aperture to selectively restrict the volume of air entering and exiting said body portion and said mouthpiece, said restriction means being adapted to be adjusted by the user by opening and closing the users mouth against said mouthpiece;

operatively interconnecting said mouthpiece to said restriction means;

inserting said mouthpiece into the mouth and inhaling and exhaling into said mouthpiece;

simultaneously inhaling and exhaling through said mouthpiece while adjusting said air restriction means by opening and closing the mouth to increase and decrease the volume of air entering and exiting said body portion and said mouthpiece.

29. The method of claim 28, further including the following step:

rotating said restriction means by opening and closing the mouth.

30. The method of claim 29 further including the steps of:

forming at least one elongated laterally extending slot in said air restriction means;

forming at least one elongated laterally extending aperture in said body portion;

passing said at least one slot over said at least one aperture to rapidly adjust the volume of air entering and exiting said main body.

31. The method of claim 29, further including the steps of:

squeezing the mouthpiece with the mouth;

holding the mouthpiece in the squeezed position;

inhaling and exhaling through the squeezed mouthpiece.

32. The method of claim 29, further including the steps of:

inhaling and exhaling through the mouthpiece while opening and closing the mouth to adjust the restriction means;

building up air pressure in the lungs when said air restriction means is decreasing the volume of air entering and exiting the mouthpiece;

relieving the air pressure built up in the lungs when said air restriction means is increasing the volume of air entering and exiting the mouthpiece;

thereby providing bursts of air through said body portion and said mouthpiece to percuss the user's lungs.

33. The method of claim 28, further including the steps of:

squeezing the mouthpiece with the mouth;

holding the mouthpiece in the squeezed position;

inhaling and exhaling through the squeezed mouthpiece.

34. The method of claim 28, further including the following steps:

squeezing the mouthpiece with the mouth and holding the mouthpiece in the squeezed position to either inhale or exhale;

adjusting the pressure on the mouthpiece and holding to either inhale or exhale.

35. The method of claim 34, further including the steps of:

forming at least one elongated laterally extending slot in said air restriction means;

forming at least one elongated laterally extending aperture in said body portion;

passing said at least one slot over said at least one aperture to rapidly adjust the volume of air entering and exiting said main body.

36. The method of claim 28, further including the step of rapidly opening and closing the mouth to rapidly adjust the restriction means;

thereby providing bursts of air through said body portion and said mouthpiece to percuss the user's lungs.

37. The method of claim 36, further including the steps of:

forming at least one elongated laterally extending slot in said air restriction means;

forming at least one elongated laterally extending aperture in said body portion;

passing said at least one slot over said at least one aperture to rapidly adjust the volume of air entering and exiting said main body.

38. The method of claim 28, further including the steps of:

forming at least one elongated laterally extending slot in said air restriction means;

forming at least one elongated laterally extending aperture in said body portion;

passing said at least one slot over said at least one aperture to rapidly adjust the volume of air entering and exiting said main body.

39. A method for exercising the lungs of a user, said method comprising the steps of:

providing a mouth adjustable lung exercising apparatus having a mouthpiece and a restriction means;

operatively interconnecting said mouthpiece to said restriction means;

inserting said mouthpiece into the mouth and inhaling and exhaling through said mouthpiece;

manipulating said mouthpiece to adjust said air restriction means to increase and decrease the volume of air entering and exiting said mouthpiece while inhaling and exhaling through said mouthpiece; and rapidly opening and closing the mouth to rapidly adjust the restriction means;

thereby providing bursts of air through said body portion and said mouthpiece to percuss the user's lungs.

* * * * *